(12) United States Patent
Ollivier

(10) Patent No.: US 11,351,385 B2
(45) Date of Patent: Jun. 7, 2022

(54) ATTACHMENT MEANS FOR IMPLANTABLE CARDIAC DEVICE

(71) Applicant: SORIN CRM SAS, Clamart (FR)

(72) Inventor: Jean-Francois Ollivier, Gif sur Yvette (FR)

(73) Assignee: Sorin CRM SAS, Clamart (FR)

( * ) Notice: Subject to any disclaimer, the term of this patent is extended or adjusted under 35 U.S.C. 154(b) by 38 days.

(21) Appl. No.: 16/128,407

(22) Filed: Sep. 11, 2018

(65) Prior Publication Data

US 2019/0076664 A1   Mar. 14, 2019

(30) Foreign Application Priority Data

Sep. 14, 2017   (EP) ..................................... 17306184

(51) Int. Cl.
| | | |
|---|---|---|
| *A61N 1/375* | (2006.01) | |
| *A61N 1/05* | (2006.01) | |
| *A61N 1/362* | (2006.01) | |
| *A61N 1/39* | (2006.01) | |

(52) U.S. Cl.
CPC ......... *A61N 1/37518* (2017.08); *A61N 1/059* (2013.01); *A61N 1/0573* (2013.01); *A61N 1/362* (2013.01); *A61N 1/3756* (2013.01); *A61N 1/37512* (2017.08); *A61N 1/0575* (2013.01); *A61N 1/3968* (2013.01)

(58) Field of Classification Search
CPC ............ A61N 1/37518; A61N 1/37512; A61N 1/0573; A61N 1/059; A61N 1/362; A61N 1/3756; A61N 1/0575; A61N 1/3968
See application file for complete search history.

(56) References Cited

U.S. PATENT DOCUMENTS

| | | | |
|---|---|---|---|
| 6,141,588 A * | 10/2000 | Cox | A61N 1/3622 128/903 |
| 7,899,550 B1 | 3/2011 | Doan et al. | |
| 9,242,102 B2 | 1/2016 | Khairkhahan et al. | |
| 2009/0082827 A1* | 3/2009 | Kveen | A61N 1/375 607/36 |
| 2012/0158111 A1* | 6/2012 | Khairkhahan | A61N 1/37205 607/127 |
| 2012/0191169 A1 | 7/2012 | Rothstein et al. | |
| 2015/0374493 A1* | 12/2015 | Yaron | A61F 2/2445 623/2.36 |
| 2015/0374976 A1* | 12/2015 | Regnier | B23K 26/21 607/120 |

(Continued)

FOREIGN PATENT DOCUMENTS

| | | | | |
|---|---|---|---|---|
| CN | 107583187 | * | 1/2018 | ............... A61N 1/05 |
| EP | 1 040 846 A1 | | 10/2000 | |

(Continued)

OTHER PUBLICATIONS

European Search Report on European Application No. 17306184.7 dated Feb. 2, 2018. 7 pages.

(Continued)

*Primary Examiner* — Catherine M Voorhees
*Assistant Examiner* — Roland Dinga
(74) *Attorney, Agent, or Firm* — Foley & Lardner LLP

(57) ABSTRACT

The present invention relates to an implantable cardiac device. The implantable cardiac device comprises a planar spiral for attaching the implantable cardiac device to a patient's tissue.

19 Claims, 9 Drawing Sheets

(56) References Cited

U.S. PATENT DOCUMENTS

2016/0310726 A1* 10/2016 Demmer ............ A61N 1/37211

FOREIGN PATENT DOCUMENTS

| EP | 1 321 165 A2 | 6/2003 |
| EP | 2 789 368 A1 | 10/2014 |
| GB | 1 371 033 A | 10/1974 |
| WO | WO-2012/051235 A1 | 4/2012 |

OTHER PUBLICATIONS

Office Action on European Application No. 17306184.7 dated Feb. 27, 2020, 5 pages.

* cited by examiner

ATTACHMENT MEANS FOR IMPLANTABLE CARDIAC DEVICE

CROSS-REFERENCE TO RELATED PATENT APPLICATIONS

This application claims the benefit of and priority to European Application No. 17306184.7, filed Sep. 14, 2017, which is incorporated herein by reference in its entirety.

BACKGROUND

The present invention relates to an attachment means for an implantable cardiac device, in particular to an implantable cardiac device affixed to patient's tissue by means of a screw.

Implantable cardiac devices, like a pace maker or defibrillator, are used to continuously monitor heart rhythms and to deliver, if needed, electrical stimulation, including pacing, resynchronization, and/or defibrillation pulses to the heart. In use, at least a part of an implantable cardiac device is affixed to and secured in the heart chamber, such as the right or left atrium or ventricle, of a patient.

Traditional implantable cardiac devices comprise a housing positioned outside the heart chamber and a probe connected to the housing at a proximal end and attached inside the heart chamber at a distal end. More recent devices no longer make use of these two parts, but integrate all functionalities into one so called leadless capsule. Such a capsule is known from EP2959940A1. FIG. 1 illustrates this leadless capsule 10 with a body 12 housing the main components of the device, including electronic circuits, power source, stimulation electrodes, etc., and a distal end portion 14 with an electrode 16 and a fixing means 18. The fixing means 18 ensures a reliable attachment to the tissue and presses the electrode 16 against the wall of the heart chamber. The fixing means 18 is formed by a projecting helically wound wire mounted on a screw support 20 incorporating recesses 22 at the circumference. The recesses 22 reduce the risk of an unwanted detachment by squeezing heart tissue into the recesses 22.

EP1040846A1 discloses tines as an alternative attachment means.

During the implanting of the cardiac device 10, a practitioner applies a torque, using a catheter, to rotate the helical screw 18 into the heart muscle and to bring the electrode 16 into contact with the excitable cells of the cardiac wall.

The helical screw 18 used for implanting the cardiac device 10, described in the state of the art, requires a minimum active length H0, where the minimum activation length H0 is the distance between the tip 24 of the helical screw 18 and the surface of the screw support 20. Typically, the active length L is on the order of 1.5 mm to 2 mm.

However, during the implanting of the cardiac device 10, there remains a risk of an unintentional perforation of the cardiac wall. The risk of perforation is related to the length of the helical screw 18 (or the tines in the alternative attachment means); especially where the cardiac wall is relatively thin, such as the right ventricle, and/or when uncontrolled torque is applied during implantation of the cardiac device 10.

SUMMARY

In view of the above, it is an object of the present invention to provide an attachment means for an implantable cardiac device that overcomes the above-mentioned drawback of the art, and therefore simplifies, and improves the safety of, the attachment of the cardiac device by the operator.

The above-mentioned problem is addressed by an implantable cardiac device comprising a planar spiral attachment means for attaching the implantable cardiac device to a patient's tissue, according to claim 1. The object of the present invention is achieved by using a planar spiral screw which achieves the attachment by squeezing cardiac tissue between the spires of the planar attachment means without having to penetrate deeply into the tissue. Thus, the active length of the screw can be reduced in comparison with a projecting helical screw extending axially from the device body, as described by the state of the art. Hence, the risk of a cardiac tamponade due to an accidental perforation of the cardiac wall by the screw is reduced, while the anchoring efficiency is maintained.

The implantable cardiac device can be further improved according to various advantageous embodiments.

In one embodiment, the implantable device may further comprise a housing with a distal end portion, wherein the planar spiral attachment means is located at the distal end portion, in particular, the planar spiral attachment means is laying over the surface of the distal end portion. Thereby, the active length of the planar spiral attachment means can be kept low.

According to an embodiment, the implantable device may comprise an electrode on the surface of the distal end portion wherein, in particular, the electrode is positioned in the center of the planar spiral attachment means. The positioning of the electrode into the center of the spiral screw allows the reliable delivery of electrical signals to and the reliable receiving of electrical signals from cardiac tissue by the electrode. Furthermore, unlike conventional screws previously described in the state of the art, the screwing of the planar spiral concentrically tracts the tissues towards the electrode, which reduces or even removes permanent tensile stress applied on the tissues in the area of the electrode. Therefore, by preserving the viability of the cells in contact with the electrode, the electrical performance of the device is ensured. Indeed, it is necessary to keep the cells of the cardiac wall surrounding the electrode of the implantable cardiac device alive and viable to ensure the excitation of the cells.

According to an embodiment, the electrode can have a shape of a disc or a half-sphere centered on the surface of the distal end portion protruding outwardly with respect to the surface of the distal end portion. This improves the contact between the electrode and the cardiac tissue.

According to an embodiment, the distances between successive turnings of the planar spiral attachment means can increase from the inner most center point of the spiral towards the end of the spiral at least over a partial range of the spiral. The changing distance allows an increasing compression of the successive turnings of the planar spiral towards the center and thus increases the friction of the spiral with cardiac tissue. Therefore, the anchoring efficiency of the planar spiral attachment means is improved.

According to an embodiment, the outermost end of the planar spiral attachment means may be shaped in order to be able to puncture and/or to penetrate at least the endothelium of the cardiac tissue. In particular, the outermost end of the planar spiral attachment means is preferentially refined, usually by machining, in two planes, creating a perforating, but not sharp tip. Even more in particular, the perforating features of the tip lies essentially in the plane of the spiral. The purpose of this tip is to allow crossing the endothelium and to penetrate the cardiac muscle, while keeping tissue damage low. A significant advantage of this single perforating tip over attachment means using tines or barbs, usually comprising four tines, is that only one puncture is performed in the endothelium for the positioning of the present device.

According to an embodiment, the planar spiral attachment means may comprise a radially expandable spiral able to extend in diameter when screwed into the patient's cardiac tissue. The radially expandable spiral ensures attachment in a horizontal plane parallel to the fixation wall and just underneath the endothelium. Furthermore, this advantageous embodiment increases the surface region of the endothelium that is in direct contact with the spiral attachment means and thus, can help to reduce the stress on the tissue under traction of the device caused by the beating of the heart.

In a variant, the planar spiral attachment means can be expandable radially beyond the area of the surface, or diameter, of the distal end portion. This advantageous variant increases the distance between tissues potentially damaged under tensile stress as well as the cardiac tissue pinched between the successive turnings of the spiral from the electrode and therefore, increases the distance of the electrode from non-viable cells. Furthermore, in this variant, the interacting surface of the endothelium with the attachment means is enlarged, which improves the anchoring of the device.

In a further variant, the planar spiral attachment means can be essentially made of a metal alloy of Nickel and Titanium, in particular, made of Nitinol. Indeed, the superelasticity of Nitinol permits the self-expansion of the planar spiral attachment into cardiac tissue during rotation.

According to an embodiment, the cross-section of the turnings of the planar spiral attachment means can be essentially rectangular. This advantageous embodiment allows enlarging the projected area of the planar spiral surface with respect to the cardiac tissue.

According to an embodiment, the cross-section of the turnings of the planar spiral attachment means can radially decrease from the inside to the outside. The variable thickness of the wire spiral progressively increases the wire stiffness and thereby improves the stability of the attachment.

According to an embodiment, the spiral attachment means may comprise two or more planar spirals embedded in each other. In this embodiment, the endothelium is wedged between the two (or more) spirals ensuring a progressive pinch effect of the endothelium and therefore further improving the attachment of the device into the endothelium or the muscle.

In another embodiment, the spirals can also be placed on top of each other. In this variant, the tissue can also be squeezed between the spires to further improve the attachment properties.

According to an embodiment, at least a portion of the planar spiral screw can be an electrode. Thus, the design of the end portion can be simplified.

According to an embodiment, the implantable cardiac device can further comprise a collar carrying a steroid agent, mounted in an area located at the distal end portion and in the vicinity of the electrode area. The steroid agent prevents the formation of fibrosis that could damage the efficiency of the implantable cardiac device.

According to an embodiment, the implantable cardiac device can be a cardiac pacing or defibrillating device with or without wired leads, in particular, a leadless capsule for cardiac stimulation and/or an epicardial implantable cardiac device.

According to an embodiment, the surface of the distal end portion can comprises a protrusion or bump facing the spiral in the vicinity of the outermost end of the spiral. This protrusion can prevent the bending down of the spiral under the counter force of the cardiac tissue and can also serve to prevent unwanted unscrewing of the implantable device.

According to an embodiment, the planar spiral attachment means is attached to the housing of the implantable cardiac device towards the center of the surface of the distal end portion. In this case, the puncturing of the patent's tissue will occur away from the electrode.

According to a variant, the planar spiral attachment means is attached towards the outer edge of the surface of the distal end portion of the housing. Therefore, the strongest squeezing of the patient's tissue occurs far away from the electrode.

According to an embodiment, the surface of the distal end portion has a rotationally symmetric convex, in particular beveled or rounded, shape. According to a further variant, the planar spiral attachments means can also have a convex shape such that the exterior extremity of the planar spiral attachment means is bent towards the surface of the distal end portion.

BRIEF DESCRIPTION OF THE DRAWINGS

Additional features and advantages will be described with reference to the drawings. In the description, reference is made to the accompanying figures that are meant to illustrate preferred embodiments of the invention. It is understood that such embodiments do not represent the full scope of the invention.

DETAILED DESCRIPTION

Figure 1:
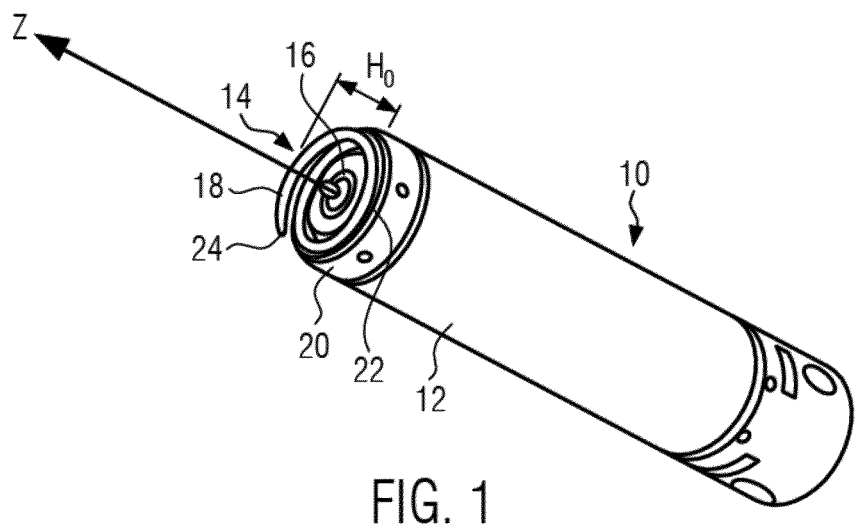
FIG. 1 illustrates an implantable cardiac device provided with projecting helical screw according to the prior art.

The present invention will now be described with reference to the attached figures. Various structures, systems and devices are schematically depicted in the drawings for purposes of explanation only and so as to not obscure the present disclosure with details which are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary or customary meaning as understood by those skilled in the art, is intended to be implied by consistent usage of the term or phrase herein.

The following embodiments are described in sufficient detail to enable those skilled in the art to make use of the invention. It is to be understood that other embodiments would be evident, based on the present disclosure, and that system, structure, process or mechanical changes may be made without departing from the scope of the present disclosure. In the following description, numeral-specific details are given to provide a thorough understanding of the disclosure. However, it would be apparent that the embodiments of the disclosure may be practiced without the specific details. In order to avoid obscuring the present disclosure, some well-known circuits, system configurations, structure configurations and process steps are not disclosed in detail.

Figure 2:
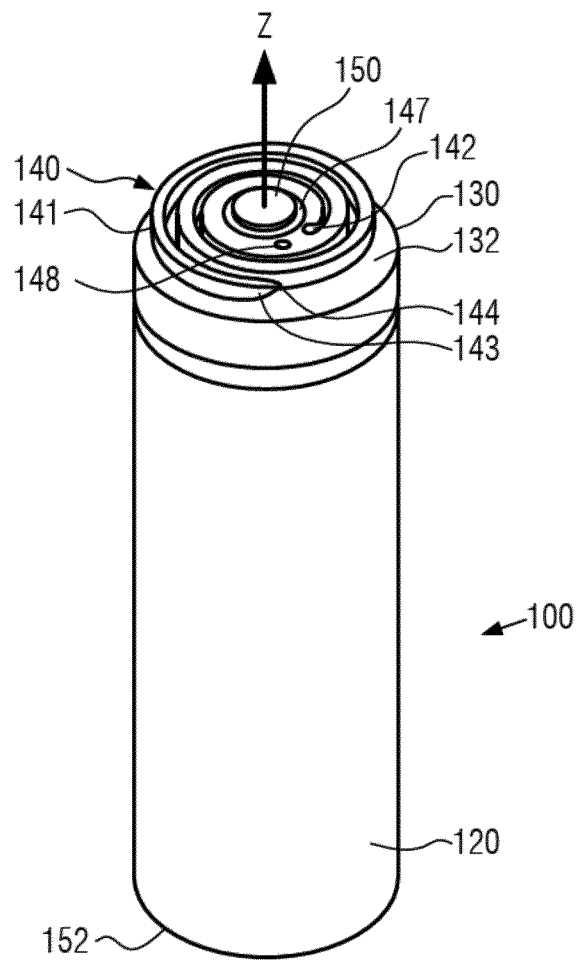
FIG. 2 illustrates schematically an implantable cardiac device provided with a planar spiral attachment means according to a first embodiment.

An attachment means for implantable cardiac device, in particular a leadless capsule for cardiac stimulation, according to a first embodiment of the present invention is schematically illustrated in FIG. 2. The implantable cardiac device 100 comprises a body 120 housing for various components of the device, such as electronic circuits and a power source. At its distal end portion 130, the implantable cardiac device 100 further comprises a planar spiral attachment means 140. The planar spiral attachment means 140 is provided over, in particular, a surface 132 of the distal end portion 130. The distal end portion 130 forms a support made of an electrically isolating material, such as a biocompatible polymer.

The planar spiral attachment means 140 has a spiral 141, e.g. a spirally wound wire, essentially centered on the surface 132 of the distal end portion 130. An inner portion 142, in particular the innermost portion, of the spiral 141 is fixed to the surface 132 of the distal end portion 130 while the remaining part up to the outermost end 143 of the spiral 141 is free. The outermost end 143 is shaped so as to present a tip 144 able to puncture a patient's tissue.

The implantable cardiac device 100 further comprises an electrode 150 centered on the surface 132 of the distal end portion 130 of the body 120. The electrode 150 represented in FIG. 2 has the shape of a disk, but could have any other suitable shape, such as a half-sphere that protrudes outwardly with respect to the surface 132 of the distal end portion 130 and outwardly with respect to the spiral 141. In use, the electrode 150 is used for sensing cardiac activity and/or for providing stimulation signals to the cardiac tissue. In another realization, not represented in FIG. 2, the device may comprise more than one electrode. For example, a second electrode, e.g. the anode, may be provided on the proximal side 152 of the body 120 for bipolar pacing and/or sensing means.

The positioning of the spiral 141 on the surface 132 is realized by centering the central hole of the spiral 141 around the protruding electrode 150, while being electrically isolated from the electrode 150, and by fixing the spiral 141 to the distal end portion 130. An insulating material 147 can be provided on the surface 132 of the distal end portion 130 between the electrode 150 and the first turn of the spiral 141 to prevent an electrical connection between the spiral 141 and the electrode 150. The spiral 141 is fixed on the surface 132 by positioning a rod that is integrally formed with the distal end portion 130 into the lateral hole 148 of the spiral 141 and welding the rod with the spiral 141.

Figure 3A:
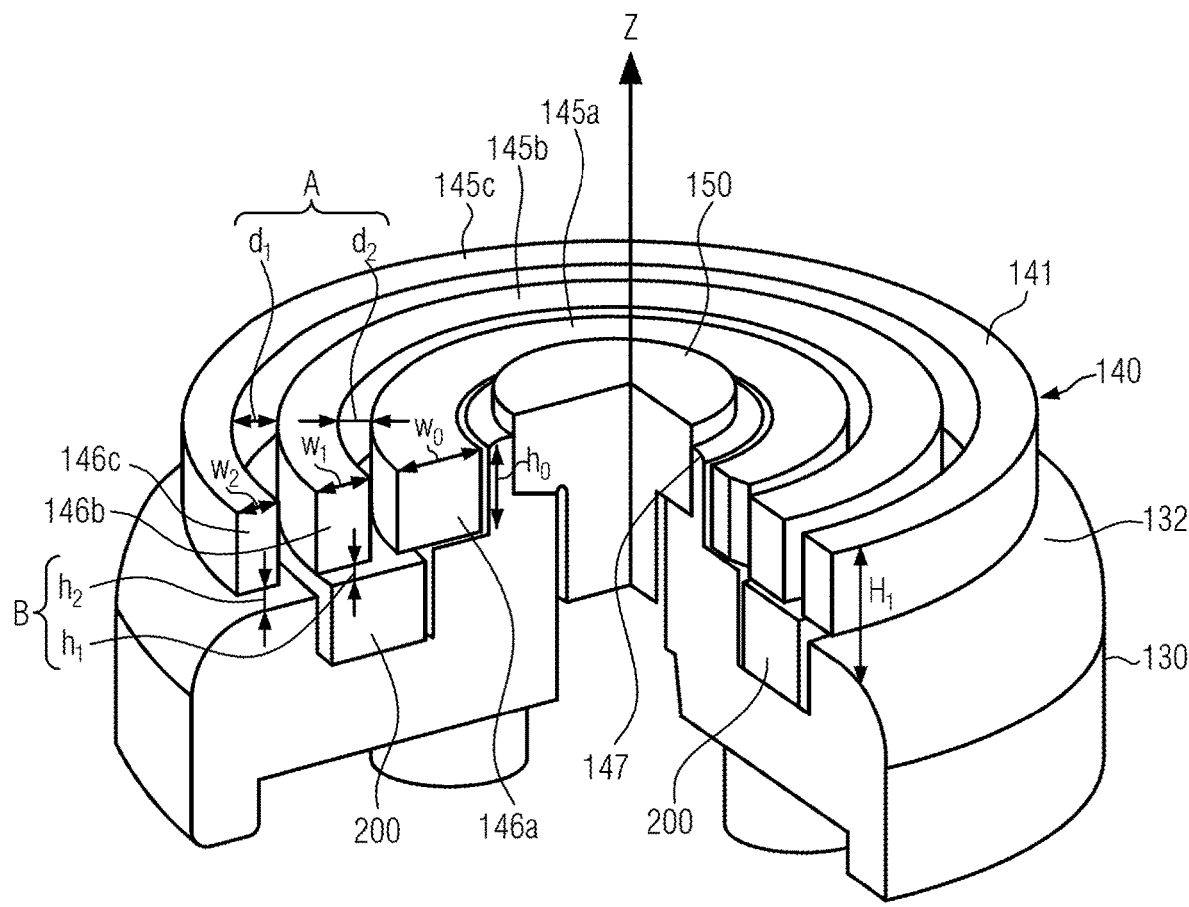
FIG. 3a illustrates a cross-section view of the planar spiral attachment means according to the first embodiment.

A partial cross-section view of the planar spiral attachment means 140 of the implantable cardiac device 100 according to the first embodiment is shown in FIG. 3a. The electrode 150 is centered on the surface 132 the distal end portion 130 and surrounded by the spiral 141.

As can be seen in FIG. 3a, the distance d1, d2 between the successive turnings 145a, 145b, 145c in zone A increase from the inner portion 142 of the spiral towards the outermost end 143 of the spiral wound wire 141. Thus, d1<d2.

Furthermore, the cross-section 146a, 146b, 146c of the spiral wound wire 141 has an essentially rectangular shape. The width w0, w1 and w2 of the cross-sections 146a, 146b, 146c respectively is radially decreasing from the inner portion 142 to the outermost end 143 of the spiral 141, whereas the height h0 of the cross-sections remains essentially constant, thus the cross-section of the spiral 141 decreases towards the outermost end 143 of the spiral 141, such that w0>w1>w2.

In a variant, the height h0 of the cross-sections decreases from the outermost end 143 to the inner portion 142 of the spiral 141 and thus, varies the stiffness of the spiral 141.

The cut out in FIG. 3a also illustrates the shape of the spiral 141 and of the surface 132 of the distal end portion 130. Whereas the spiral 141 is essentially flat and perpendicular to the longitudinal axis Z of the cardiac device 100, the surface 132 of the distal end portion 130 has a rotationally symmetric convex, in particular beveled or rounded, shape with the electrode 150 positioned at its apex. As shown in the zone B between the spiral 141 and the surface 132, the distances h1 and h2 between the spires of the spiral 141 increase towards the edge of the surface 132 such that h1<h2.

Furthermore, in a variant, a collar 200 is embedded in the surface 132 of the distal end portion 130, positioned under the spiral 141 and surrounding the immediate vicinity of the electrode 150. The collar 200 is impregnated with a steroid, such as dexamethasone. Once implanted and in contact with a patient's corporal fluids, the steroid can diffuse through the zone B and come into contact with the cardiac wall to prevent, or at least reduce, the formation of unwanted fibrosis around the implantable cardiac device 100.

Unlike the fixation means 18 in the form of a helix screw as shown in FIG. 1, the planar spiral attachment means 140 does not extend along the axis Z, but remains in a plane essentially perpendicular to axis Z. Hence, the active length H1 of the attachment means 140, i.e. the axial distance in Z direction between the outermost end 143 of the spiral wound wire 141 and the screw support surface 132, is reduced and therefore limits the risk of cardiac tamponade. As an example, for a spiral 141 of a diameter of 0.5 mm, the active length of the attachment means for a helix screw 18 has a range of 1.5 mm to 2 mm; whereas the active length for the same spiral wire wound 141 in the configuration of a planar attachment means 140 is around 0.5-0.7 mm.

The dimension of the spiral wound wire 141 are chosen such that its stiffness along the axis Z is sufficiently high so as to avoid plastic deformation of the spiral 141 in Z direction when screwing the implantable device into a patient's tissue.

It is noted that the planar spiral attachment means 140 is not limited to the realization depicted by the FIG. 3a, but other shapes remain possible as long as the spiral keeps its planar geometry.

Figure 3B:
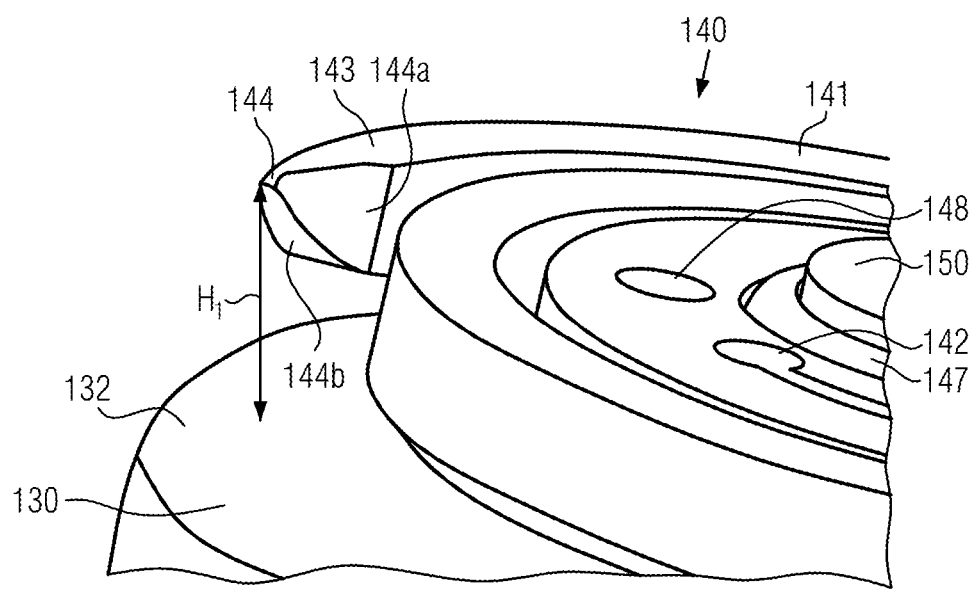
FIG. 3b illustrates an enlarged view of the outermost end of the planar spiral attachment means according to the first embodiment.

FIG. 3b is an enlargement of the outermost end 143 of the spiral 141 of the first embodiment. The outermost end 143 of the spiral is shaped as a tip 144 able to puncture the endothelium of a patient's tissue. Preferentially, the tip 144 has been sharpened along two planes, a radial plane 144a and an oblique plane 144b in order to create a perforating, but not sharp, tip 144. This corresponds to a shape that reduces the risk of tissue damage. In particular, the tip 144 essentially remains perpendicular to axis Z.

Furthermore, the shape of the tip 144 represented in FIG. 3b controls the puncture insertion depth because the depth is fixed by the maximum distance between the top of the tip 144 and the surface 132 of the distal end portion 130.

The spiral wound wire 141 can be manufactured by laser cutting a metal sheet followed by deburring. Using this technique, the desired geometry of the spiral can be obtained.

Figure 3C:
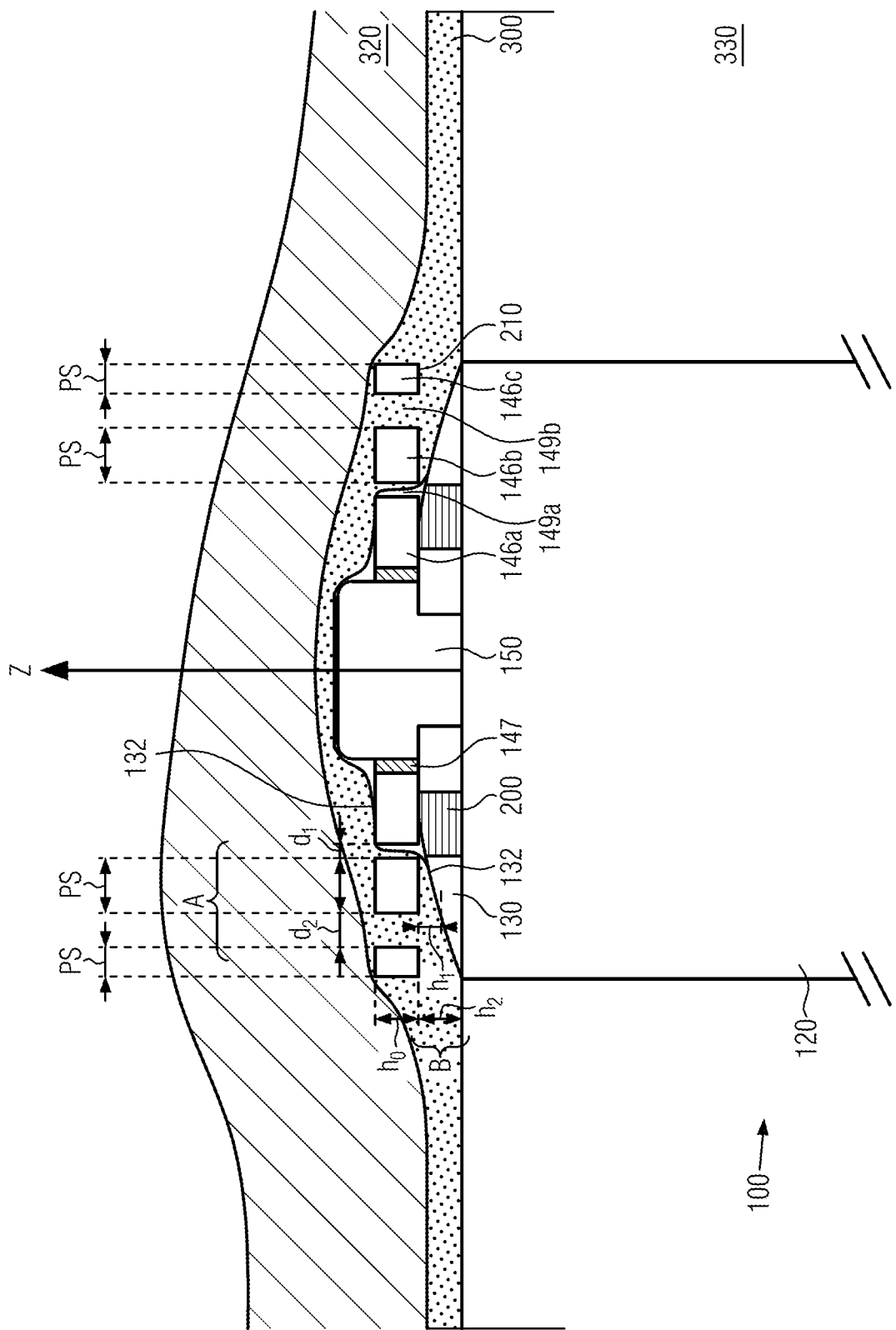
FIG. 3c illustrates a cross-section view of the implantable cardiac device according to the first embodiment attached to the endothelium.

The cross-section view represented in FIG. 3c, illustrates the implantable cardiac device 100 according to the first embodiment attached to the patient's cardiac tissue.

The cardiac tissue comprises at its inner surface towards the inside of the heart the endothelium 300 and below the endothelium the muscle tissue 320. The endothelium 300 has a thickness of about 2 mm, whereas the muscle tissue 320 can be thicker, as illustrated. The endothelium 300 has a higher mechanical resistance compared to the muscle tissue 320, and therefore, it is considered sufficient to attach the implantable cardiac device 100 essentially to the endothelium 300. It is thus not important to enter deeply into the muscle tissue 320 to obtain the desired attachment force for the cardiac device 100. It is a sufficiently large projected surface PS of the spiral 141 onto the endothelium 300 that is responsible for the retention of the cardiac device 100.

In FIG. 3c, the planar spiral attachment means 140 penetrates only into the endothelium 300. The planar attachment means 140 could, however, also penetrate at least partially into the muscle layer 320, and therefore, could also lie underneath the endothelium 300.

For implanting the cardiac device 100, the practitioner positions the distal end portion 130 of the device 100 on the endothelium 300 while the body housing 120 of the device 100 is pointing outwardly into the heart cavity 330.

Forward pressure applied by the practitioner causes the tip 144 of the spiral 141 to puncture the endothelium 300, or at least puts the tip 144 in a position to puncture the endothelium 300 as the device begins to rotate. By rotating the cardiac device around its axis, e.g. by one and half turns, the planar attachment means 140 screws into the endothelium 300. The screwing of the planar spiral 141 concentrically tracts the tissues of the endothelium 300 towards the electrode 150, while the friction between the spiral 141 and the cardiac tissue increases with respect to the successive turns. Finally, the spiral 141 is localized inside the endothelium 300, while the electrode 150 is pressed against the surface of the endothelium 300.

Therefore, the attachment of the implantable cardiac device 100 is achieved in part by wedging cardiac tissue between the spires 149a and 149b of the spiral 141, as well as between the surface support 132 and the proximal surface 210 of the spiral 141. As illustrated in FIG. 3c, the length of d1 and d2, as well as h1 and h2 increase from the inner portion of the spiral towards the outer end of the spiral.

Thus, the attachment of the implantable cardiac device 100 is achieved by establishing friction between the spiral 141 and the endothelium 300.

The attachment properties that can be achieved with the implantable cardiac device 100 are such that anti-unscrewing features, such as recess 22 like in the prior art represented in FIG. 1, can be omitted so that a potential damage of the patient's tissue by such recess cannot occur. Nevertheless it still remains possible to use such anti-unscrewing features as well.

The projected surface PS corresponds to the surface area of the winding of the spiral 141 positioned inside the endothelium 300, thus the part of the tissue that has the mechanical properties to ensure the attachment, and in a plane perpendicular to the Z direction. The dimension of the wire used for the spiral 141, like the cross-section 146a, 146b, 146c and its height h0, are preferentially adapted to enhance the projected surface PS with the endothelium 300. As an example, in FIG. 3c, the projected surface PS is about 6 mm$^2$.

Furthermore, as it can be seen in FIG. 3c, the cross-section 146a, 146b, 146c of the spiral 141 has an essential rectangular shape which enlarges the projected area PS of the spiral 141 in direct contact with cardiac tissue. This will further improve the attachment of the device 100.

Figure 4A:
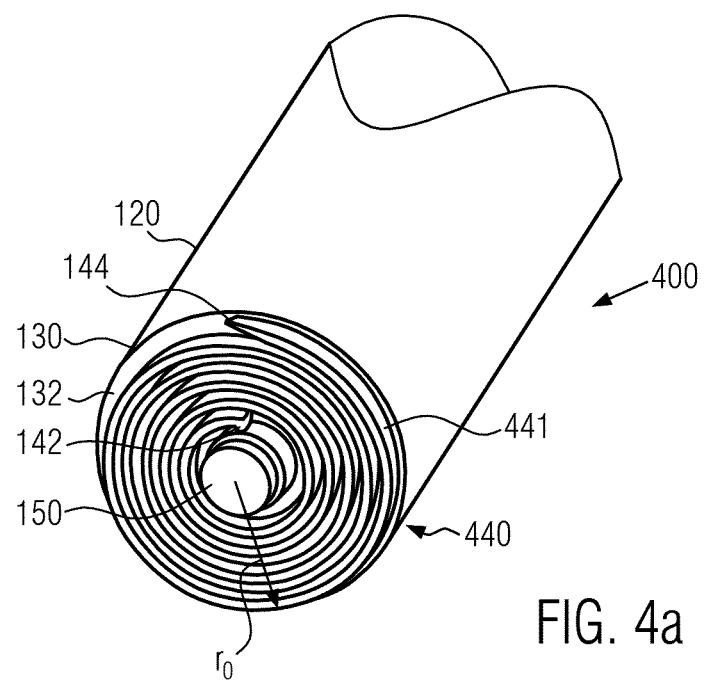
FIG. 4a illustrates an implantable cardiac device according to a second embodiment prior to the attachment in a patient's tissue.
Figure 4B:
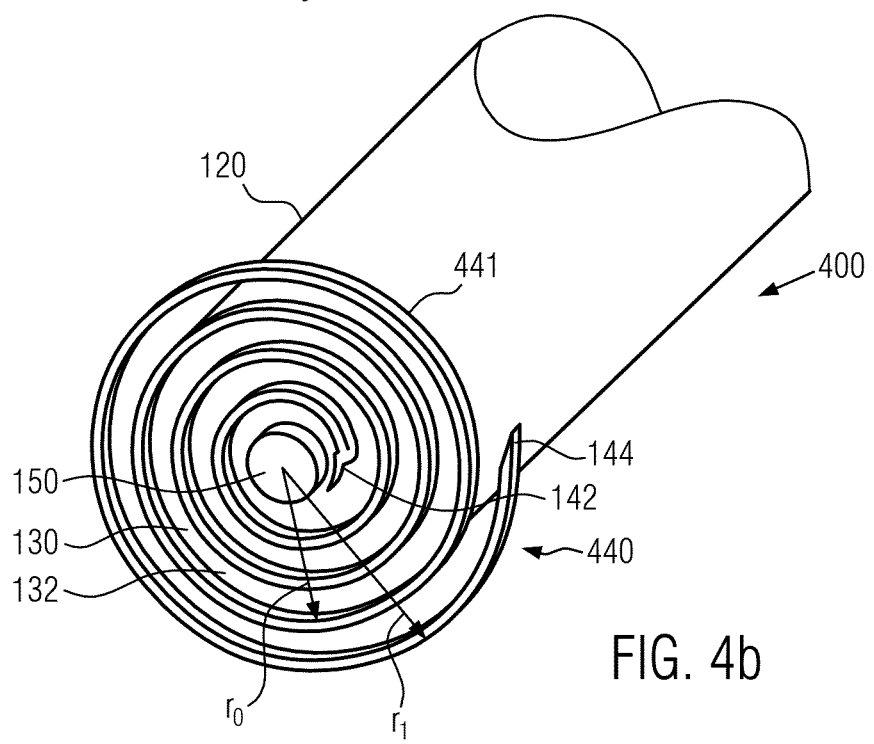
FIG. 4b illustrates the implantable cardiac device according to a second embodiment when the device is attached to a patient's tissue.
Figure 4C:
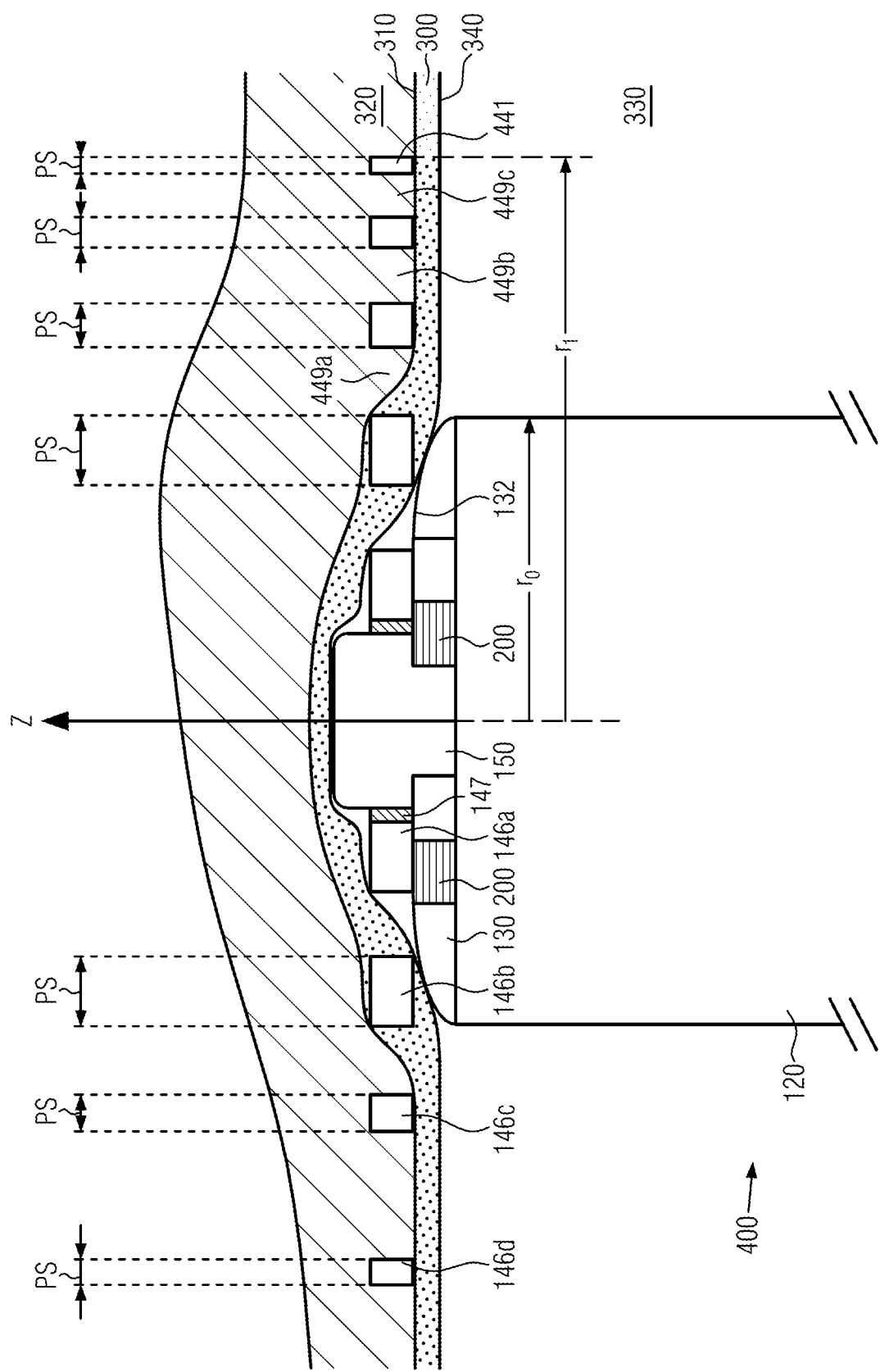
FIG. 4c illustrates a cross-section view of the implantable cardiac device attached to a patient's tissue according to the second embodiment.

FIGS. 4a to 4c depict an implantable cardiac device according to a second embodiment, wherein the planar spiral attachment means is radially expandable in its plane.

FIG. 4a illustrates an implantable cardiac device 400 comprising a planar spiral attachment means 440 according to a second embodiment in a state prior to attachment into a patient's tissue. The only difference between the implantable cardiac device 400 of the second embodiment and the one of the first embodiment is the use of a different planar spiral attachment means 440. The remaining features of the cardiac device 400, having reference numerals already used, will therefore not be explained in detail again, reference is made to their earlier description.

Indeed, the planar spiral attachment means 440 is configured to be radially expandable from its initial radius r0, essentially corresponding to the radius of the housing of the cardiac device to a larger radius. Although in some variants, r0 may be smaller or larger that the radius of the housing. In order to render the planar spiral attachment means 440 expandable, the spiral 441 of the planar spiral attachment means 440 is preferentially made of a superelastic alloy, such as Nitinol for example, which in particular, exhibits a range of yield strength values between 70 and 700 MPa and a range of Young's modulus values between 30 to 80 GPa.

FIG. 4b illustrates the implantable cardiac device 400 once attached to the patient's tissue. As can be seen, the planar spiral attachment means 440 is expanded with the radius of the spiral 441 increased from its initial radius r0 to a larger radius r1, thus r1>r0. Therefore, the extended spiral 441 extends beyond the area of surface 132 of the distal end portion 130 and of the housing 120 of the cardiac device 400. Typically, the radius r1 is about one and a half or two times larger than the initial radius r0. This allows increasing the distance between tissues potentially damaged by the screwing from the electrode 150 and therefore, increases the distance of the electrode 150 from non-viable tissue cells.

FIG. 4c illustrates a cross-section view of the implantable cardiac device 400 and the cardiac tissue. The cross-section 146a, close to the position where the spiral 441 is attached to the housing 120, and the electrode 150 are pressed against the external surface 340 of the endothelium 300. Further away from the center of the spiral 441, the cross-section 146b is already localized inside the endothelium 300; while even further towards the edge 134 of the surface 132 of the distal end portion 130, the cross-sections 146c, 146d of the spiral 441 are localized inside the muscle area 320, essentially at the interface 310 with the endothelium 300. The planar spiral attachment means 441 could also only penetrate into the endothelium 300, as illustrated in FIG. 3c of the first embodiment.

As previously described in FIG. 3c, for implanting the cardiac device 400, the practitioner has to position the distal end portion 130 of the device 400 on the endothelium 300 while the body housing 120 of the device 400 is pointing outwardly into the heart cavity 330.

Forward pressure applied by the practitioner causes the tip 144 of the spiral 441 to puncture the endothelium 300, or at least puts the tip 144 in a position to puncture the endothelium 300 as the device begins to rotate. By rotating the cardiac device 400 around its axis, e.g. by one and half turns or more, the planar attachment means 440 screws into the endothelium 300 and the tip 144 reaches into the muscle 320. Thus, except for the parts attached to surface 132, a large portion of the planar spiral 441 lies within the endothelium 300 and underneath the interface 310 of the endothelium 300 within the muscle region 320. Under the screwing effect, the tissue applies a sufficient force on the planar spiral 441 to expand it until it reaches the radius r1.

Furthermore, the electrode 150 presses firmly on the surface 340 of the endothelium 300 while the cardiac tissue between the successive turns 449a, 449b, 449c of the spiral 441 is localized on the interface 310, in the muscle 320 just underneath the endothelium 300. Therefore, the electrode 150 is kept away from the cardiac tissue under stress from, and potentially damaged by, the embedded planar spiral 141.

FIGS. 5a to 5g illustrate further embodiments of the invention. Only the differences with respect to the first embodiment will be described. Thus, features with reference numerals already used above will not be described in detail, but reference is made to their description.

Figure 5A:
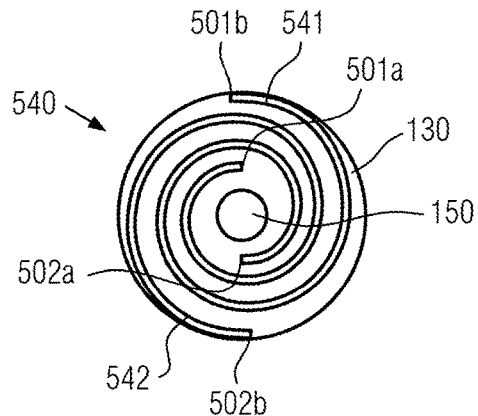
FIGS. 5a to 5g illustrate further embodiments of the implantable cardiac device.

FIG. 5a illustrates a third embodiment wherein the planar attachment means 540 comprises two spirals, 541 and 542, fixed near the center of the distal end portion 130 and surrounding the electrode 150. The terminal ends 501a, 501b of the spiral 541 are diametrically opposed to the terminal end 502a, 502b of the spiral 542. In this embodiment, the cardiac tissue, which is not represented in FIG. 5, is squeezed between the two spirals 541, 542 ensuring a progressive pinch effect of the cardiac tissue, and therefore, further improving the attachment of the device.

Figure 5B:
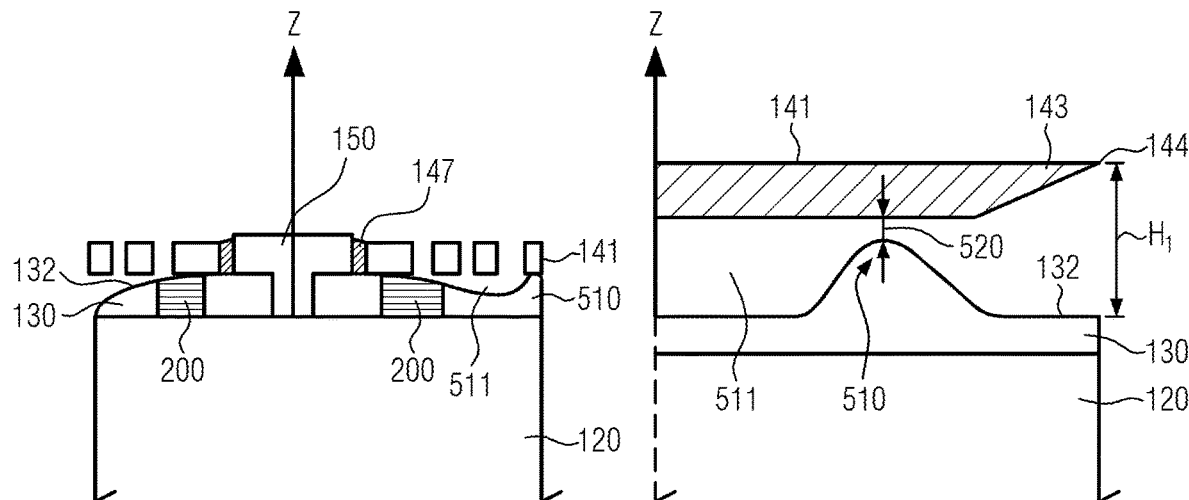

According to a fourth embodiment, illustrated in FIG. 5b, a protrusion or bump 510 is provided on the surface 132 of the distal end portion 130 in the vicinity of the external terminal end 143 of the spiral 141, e.g. from about 0 mm to about 0.8 mm of the terminal end 143. The spiral 141 can thus come to a rest on the bump 510 during the puncturing into a patient's tissue. The bump 510 can prevent the bending down of the spiral 141 in the negative Z direction under the counter force of the tissue. Preventing the bending down of the spiral 141 eases the puncturing operation, and reduces the likelihood that the penetration depth of the spiral 141 into the patient's tissue is too low, in which case the attachment to the patient's tissue would not be sufficiently strong. After attachment of the spiral 141 to the cardiac tissue, the bump 510 secures the cardiac tissue in zone 511 between the inner part of the surface 132 and the spiral 141, and therefore, reduces the risk of unwanted un-screwing of the cardiac device 100.

Furthermore, during the rotation to affix the cardiac device 100, the cardiac cells will only be briefly squeezed in the thin zone 520 between the spiral 141 and the bump 510, and thus the potential for damage to the cells can be reduced.

Figure 5C:
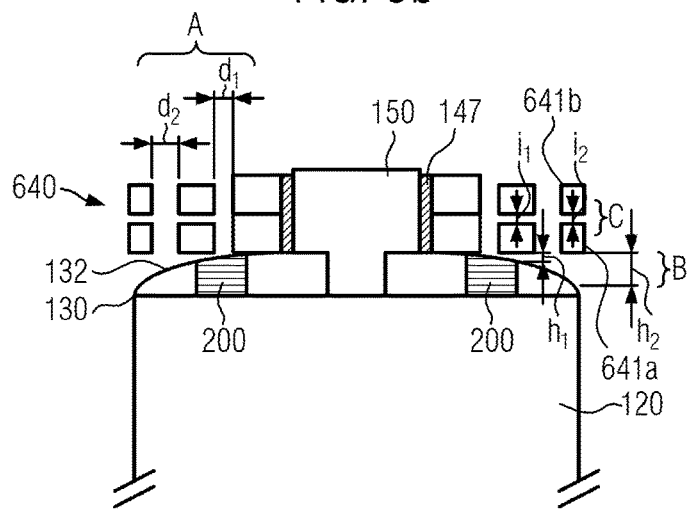

According to a fifth embodiment, illustrated in FIG. 5c, the planar attachment means 640 comprises two spirals 641a and 641b on top of each other. During the screwing of the planar attachment means 640, the tissue is tracked and squeezed between zones A and B, as previously described in FIG. 3a, as well as between the two spirals 641a, 641b delimiting a zone C. The height of zone C is represented by the inter-spiral height i1 and i2 on FIG. 5c. This embodiment further secures the attachment of the device by increasing the friction between the spirals 641a, 641b and the tissue. According to further variants, more than two spirals could be provided.

Figure 5D:
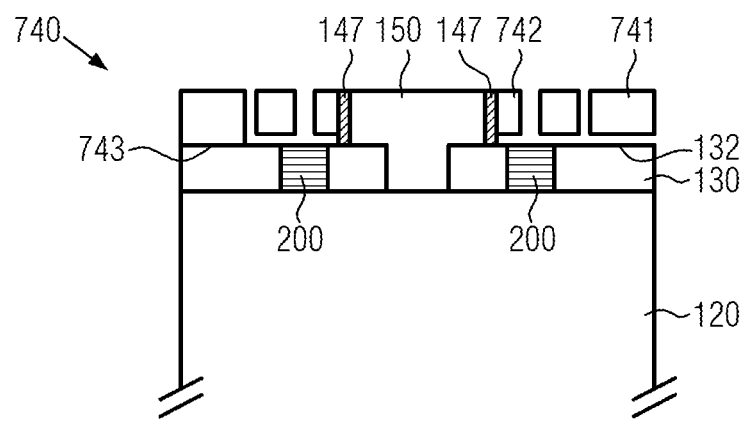

According to a sixth embodiment, illustrated in FIG. 5d, the planar attachments means 740 comprises an eccentric spiral 741 attached on the outer edge of the surface 132 of the distal end portion 130. In contrast to the other embodiments, the inner point 742 of the spiral 741 is free and surrounding the electrode 150 whereas the outer point 743 of the spiral 741 is fixed to the support 132. The puncture site, after the cardiac device is attached to the cardiac tissue, is therefore, spaced further away from the electrode 150.

Figure 5E:
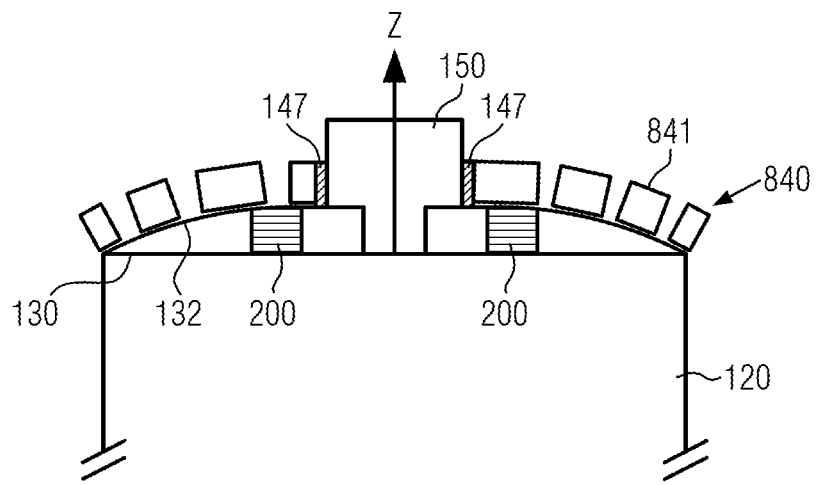

According to a seventh embodiment, illustrated in FIG. 5e, the planar attachments means 840 comprises a spiral 841 bending downwardly in the direction of Z negative toward the surface 132 of the distal end portion 130.

Figure 5F:
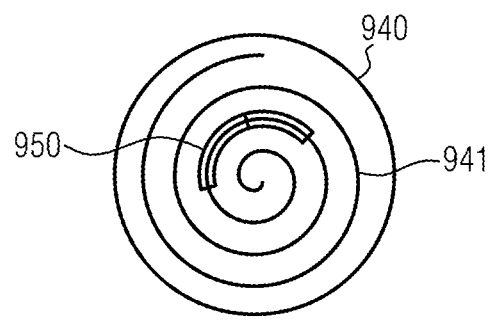

According to an eighth embodiment, illustrated in FIG. 5f, the planar attachments means 940 comprises a spiral 941, wherein a part of the spiral 941 is the electrode 950.

Figure 5G:
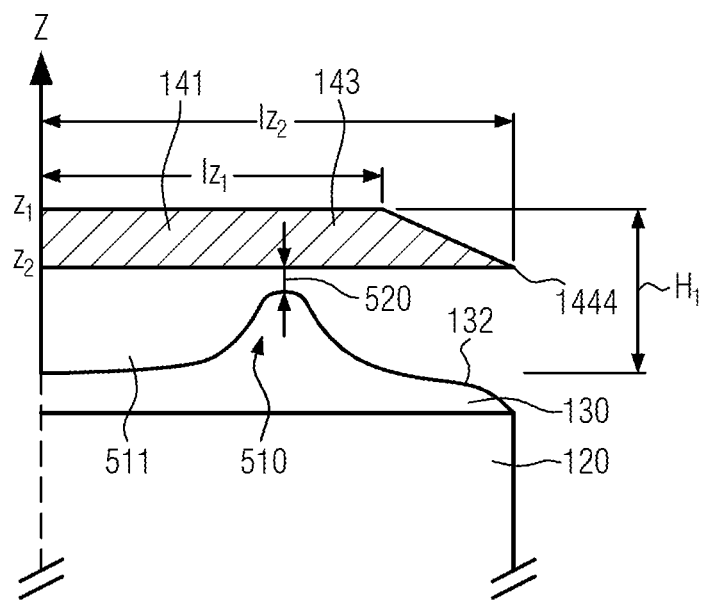

According to a ninth embodiment, illustrated in FIG. 5g, the outermost end 143 of the spiral 141 comprises a tip 1444, that has been sharpened along a plane in negative Z, meaning that $l(z1) < l(z2)$ with $z1 > z2$, unlike in the embodiments shown in FIG. 3b or 5b where the tip 144 has been sharpened along a plane in positive Z.

Whereas puncturing the tissue with a tip 1444 is less easy than with a tip 144, as the tip 144 is in immediate contact with the patient's tissue; the tip 1444 has the advantage that its shape reduces the risk of an unwanted bending of the spiral along the positive Z direction. Thus, the risk of a cardiac tamponade can be further reduced.

Figure 6:
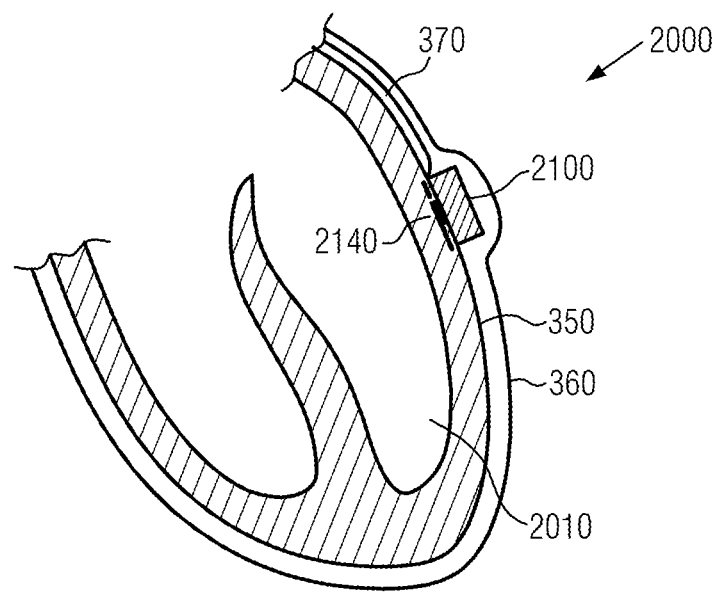
FIG. 6 illustrates schematically the attachment of an epicardial implantable cardiac device.

FIG. 6 illustrates a part of patient's heart 2000 with an epicardial implantable cardiac device 2100 according to a tenth embodiment. An epicardial implantable device 2100 may be used in particular for the stimulation of the left ventricle 2010 of the heart 2000. Again features with reference numerals already used above will not be described in detail, but reference is made to their description.

The epicardial implantable device 2100 is attached on the external wall 350 inside the pericardium 360. The attachment of the epicardial implantable device 2100 is ensured using a planar spiral attachment means 2140 embedded in the heart tissue. The planar spiral attachment means 2140 can have a shape like any one of the spirals used in the embodiments one to nine or a combination thereof with dimensions adapted to a use outside the heart 2000.

Using a planar attachment means 2140 can reduce the risk of puncturing the coronary arteries 370 compared to helical attachment means or tines as used in the prior art.

Individual features of the various embodiments previously described can be combined together to form further embodiments according to the invention, all realizing an advantageous attaching to a patient's tissue by using a planar spiral attachment means.

The invention claimed is:
1. An implantable cardiac device comprising a planar spiral structured to attach the implantable cardiac device to a patient's tissue, the planar spiral comprising a single wire formed into a plurality of successive turns and disposed in a single plane perpendicular to a longitudinal axis of the implantable cardiac device, wherein the implantable cardiac device is a cardiac pacing device for cardiac stimulation.

2. The implantable device of claim 1, further comprising a housing with a distal end portion, wherein the planar spiral is located at the distal end portion, in particular, the planar spiral is provided over a surface of the distal end portion.

3. The implantable device of claim 2, wherein the implantable device comprises an electrode on the surface of the distal end portion wherein, in particular, the electrode is positioned in the center of the planar.

4. The implantable device of claim 3, wherein the electrode is a disc or half-sphere centered on the distal end portion protruding outwardly with respect to the surface of the distal end portion.

5. The implantable device of claim 1, wherein a distance between the plurality of successive turns of the planar spiral increases from an inner portion of the spiral towards an outermost end portion of the spiral at least over a partial range of the spiral.

6. The implantable device of claim 5, wherein the outermost end portion of the planar spiral is shaped to be able to puncture and/or to penetrate at least the endothelium of the cardiac tissue.

7. The implantable device of claim 1, wherein the planar spiral comprises a radially expandable spiral able to extend in diameter when screwed into the patient's cardiac tissue.

8. The implantable device of claim 7, wherein the planar spiral is expandable radially beyond the area of the surface of the distal end portion.

9. The implantable device of claim 1, wherein the planar spiral comprises a metal alloy of Nickel and Titanium.

10. The implantable device of claim 9, wherein the planar spiral comprises Nitinol.

11. The implantable device of claim 1, wherein a cross-section of the plurality of successive turns of the planar spiral is substantially rectangular.

12. The implantable device of claim 11, wherein the cross-section of the plurality of successive turns of the planar spiral is radially decreasing from the inside to the outside at least over a partial range of the spiral.

13. The implantable device of claim 11, wherein the planar spiral is attached to the distal end portion with the center region of the planar spiral.

14. The implantable device of claim 1, wherein the planar spiral comprises two or more planar spirals embedded in each other.

15. The implantable device of claim 1, wherein at least a portion of the planar spiral is an electrode.

16. The implantable device of claim 1, further comprising a collar carrying a steroid agent, mounted in an area located at the distal end portion and in the vicinity of the electrode area.

17. The implantable device of claim 1, wherein the planar spiral comprises a helix screw, and wherein the helix screw is disposed substantially within a single plane.

18. The implantable device of claim 1, wherein the planar spiral includes spirally wound wire having an inner portion and an outer portion and comprising a plurality of successive turns, wherein the inner portion is structured to be coupled to the implantable cardiac device and the outer portion is free and structured to attach to the patient's tissue.

19. The implantable device of claim 18, wherein the plurality of successive turns are concentric and disposed substantially within a single plane.

* * * * *